US006974859B1

(12) United States Patent
Stromberg et al.

(10) Patent No.: US 6,974,859 B1
(45) Date of Patent: Dec. 13, 2005

(54) PREVENTION OF DENTAL CARIES

(76) Inventors: Nicklas Stromberg, Ragangen 6A, Umea (SE) S-903 37; Ingegerd Johansson, Svampvagen 18, Umea (SE) S-903 39

( * ) Notice: Subject to any disclaimer, the term of this patent is extended or adjusted under 35 U.S.C. 154(b) by 0 days.

(21) Appl. No.: 10/009,709

(22) PCT Filed: May 11, 2000

(86) PCT No.: PCT/SE00/00930

§ 371 (c)(1),
(2), (4) Date: Jun. 20, 2002

(87) PCT Pub. No.: WO00/69890

PCT Pub. Date: Nov. 23, 2000

(30) Foreign Application Priority Data

May 17, 1999 (SE) .................................... 9901773

(51) Int. Cl.[7] ............................................. A61K 38/00
(52) U.S. Cl. ........................ 530/300; 514/14; 514/15; 514/16; 514/17
(58) Field of Search .................... 530/300; 514/14, 514/15, 16, 17

(56) References Cited

U.S. PATENT DOCUMENTS

| 4,225,579 A | 9/1980 | Kleinberg |
| 6,084,066 A * | 7/2000 | Evans et al. ................. 530/333 |

FOREIGN PATENT DOCUMENTS

| WO | WO-94/07523 A1 | 4/1994 |
| WO | WO-99/14231 A2 | 3/1999 |
| WO | WO-00/69890 A1 | 11/2000 |

OTHER PUBLICATIONS

Yasuo Yamauchi, et al, Recombinant and Native Zymogen Forms of Human Complement/Factor D[1], Journal of Immunology, 1994, pp. 3645-3652, vol. 152.

* cited by examiner

*Primary Examiner*—Jennifer E. Graser
(74) *Attorney, Agent, or Firm*—Dickstein, Shapiro, Morin & Oshinsky, LLP.

(57) ABSTRACT

A penta- to decapeptide containing two or more Arg protecting against dental caries is comprised by the amino acid sequence GlyGlyHisProArgProProArgGlyArgProGlnGlyProProGlnGln.

Also disclosed is a composition for preventing dental caries comprising an effective amount of the peptide, and a corresponding method of use.

20 Claims, 3 Drawing Sheets

PREVENTION OF DENTAL CARIES

FIELD OF THE INVENTION

The present invention relates to a means for preventing dental caries, a corresponding method, and compositions incorporating the means.

BACKGROUND OF THE INVENTION

Proline-rich proteins (PRPs) comprise about 70% of the proteins in saliva. They can be divided into acidic, basic, and glycosylated PRPs encoded by six clustered genes on chromosome 12p13.2. PRPs are potential determinants of host susceptibility to dental caries. Large multifunctional 150-residue PRPs (Lamkin M S and Oppenheim F G, Crit Rev Oral Biol Rev 4 (1993) 251–9) are known to adsorb to hydroxyapatite surfaces and inhibit calcium phosphate precipitation, modulate hydroxyapatite crystal formation as well as mediate adhesion of commensal *Actinomyces* and *Streptococcus* species to tooth surfaces. In addition, they bind to and inactivate ingested plant polyphenols (tannins). The proline-poor N-terminal 30 residue domain confers hydroxyapatite- and calcium-binding, while the proline-rich middle/C-terminal domain binds bacteria via the ProGln-terminus and tannins via proline-rich repeats.

The polymorphism of acidic PRPs involves allelic and post-translational variants; several common allelic (large PRP-1, PRP-2, Db-s, PIF-s and Pa) and post-translational (small PRP-3, PRP-4, Db-f and PIF-f) variants have been described. In regard of biological properties the acidic PRP variants differ somewhat, and large and small acidic PRPs largely, between each other. The small 106 residue acidic PRPs resulting from proteolytic cleavage at Arg106-Gly107 display poor bacterial adhesion activity but high affinity for hydroxyapatite surfaces. Both large and small acidic PRPs are secreted from the acinus cells. After secretion, the acidic PRPs are rapidly enriched on tooth surfaces and degraded as a consequence of bacterial proteolysis. Also, multiple phosphorylated peptides reminiscent of PRPs have been identified in saliva and found to possess increased affinity for hydroxyapatite surfaces. Some studies (Kousvelari E E et al., J Dent Res 59 (1980) 1430–8), though not others (Mandel I D & Bennick A, J Dent Res 62 (1980) 943–5), have associated this proteolytic activity to gingivitis and rate of plaque formation.

Arg catabolism to ammonia has been suggested to be a characteristic of streptococcal biotypes with tooth protective properties (Andersson C et al. Infect Immun 43 (1984) 555–60; Rogers A H, Aust Dent J 35 (1990) 468–71. Wijeyeweera R L& Kleinberg, Arch Oral Biol 34 (1989) 55–64; ibid. 43–53). Actually, Arg can control the ecological relationship between *S. sanguis* and *S. mutans* (van der Hoeven J S et al., J Dent Res 63 (1984) 389–92. Rogers A H et al., Oral Microbiol Immunol 2 (1987) 172–82), and caries-susceptible and caries-resistant subjects differ in ability to raise pH after an acidification (Abelson D C & Mandel I D, J Dent Res 60 (1981) 1634–8; Kleinberg I et al., Proc. "Microbial aspects of dental caries". Sp. Supp. Microbiol. Abstracts. IRL, Washington, D.C., 1976, 433–464 pp).

Arg catabolism is present in *S. sanguis, S. gordonii, S. anginosus* and *S. mitis*, while it is absent in *S. oralis* and cariogenic *S. mutans* and *S. sobrinus* (Kilian M et al., Int J Syst Bacteriol 39 (1989) 471–484). Arg-containing peptides, notably sialin (Coulter W A et al., Biochem Soc Trans 18 (1990) 337–8) may act as a local pH-buffering agents by bacterial catabolism of Arg to ammonia via the arginine deaminase pathway (Floderus E et al., APMIS 98 (1990) 1045–52).

Degradation of acidic PRPs releases oligopeptides which are transported intra-cellularly and metabolized for nutritional reasons (Kunji E R et al., Antonie Van Leeuwenhoek 70 (1996) 187–221). Gram-negative bacteria colonizing the gingival pocket, such as *Porphyromonas gingivalis*, express a broad range of proteases in utilizing proteins as a major source of energy. In contrast, commensal streptococci and actinomycetes, which dominate on oral mucosal and tooth surfaces, express multiple glycosidases in utilizing carbohydrates as a major energy source. Nevertheless, protease and peptidase activities, such as a trypsin-like serine endoprotease in *S. oralis*, S-IgA1 proteases in *S. sanguis* and *S. oralis* and yet uncharacterized proteolytic activity, are present in *Streptococcus* and *Actinomyces* species. However, little is known about the degradation of acidic PRPs by these commensal and early colonizing bacteria.

While a vast amount of knowledge about saliva constitutents and their possible role in processes leading to dental caries has been gathered, that knowledge up to know resulted in only few practically applicable propositions of how to efficiently prevent dental caries.

OBJECTS OF THE INVENTION

It is an object of the invention to provide a means for protecting dental surfaces against caries.

It is another object of the invention to provide a corresponding method.

It is a further object of the invention to provide a composition for protecting dental surfaces against caries.

Still other objects of the invention will become apparent from the following description of the invention and preferred embodiments thereof, as well as from the appended claims.

DESCRIPTION OF THE INVENTION

The present invention is based on the insight that commensal *Actinomyces* and *Streptococcus* species transform acidic PRPs to small-size peptides, such as pentapeptides. These small-size peptides are transformed into ammonia by the action of certain oral bacteria. The ammonia thus formed protects raises the pH at the dental surface and thereby protects the surface against caries.

In this transformation Arg-containing oligopeptides are released and catabolized to ammonia at or near the dental surface. Ammonia increases the pH at the dental surface and thereby counteracts caries which is promoted by a low pH in the oral cavity.

The present invention is also based on the insight that the aforementioned transformation gives rise to peptides with terminal proline or proline-glutamine entities having affinity to dental surfaces and thus competitively protecting them.

Degradation of acidic PRPs by *Streptococcus* and *Actinomyces* species comprises the following features:
  (i) step-by-step the large 150 residue PRP-1 protein is degraded into intermediate size peptides and finally into smaller oligopeptides and amino acids. Cell-bound endoproteases with broad substrate specificities are involved in the initial stages of this degradation;
  (ii) cleavage of acidic PRPs occurs preferentially in the middle/C-terminal proline-rich 96–140 region; the 106 residue PRP-3 is relatively resistant to cleavage, PRP-3-like peptides being generated by all strains and a series of fragments in region 96–140. Both endoprotease specificity per se and intrinsic properties of acidic PRPs, such as the extended structure of proline-rich stretches, explains this regional preference of cleavage;

(iii) degradation of PRP-1 releases oligopeptides both immediately and after prolonged degradation. The immediate release of an Arg106Gly107Arg108Pro109Gln110 pentapeptide is indicated by the N-terminal 105 residue Pyr1-Pro104Pro105 and the C-terminal 40 residue Gly111-Pro149Gln105 peptides initially generated by *S. gordonii* strain SK12.

Mass spectroscopy identified a N-terminal pyroglutamatic acid (Pyr) post-translational modification of acidic PRPs that blocks sequencing by Edman degradation. The peptide structures derived from degradation of the 150 residue PRP-1 by *S. gordonii* strain SK12 indicate:

(i) the instant release of an Arg106Gly107Arg108Pro109Gln110 pentapeptide together with a N-terminal 105 residue Pyr1-Pro104Pro105 and a C-terminal 40 residue Gly111-Pro149Gln150 peptide;

(ii) the generation of multiple middle/C-terminal peptides with ProGln-termini;

(iii) the cleavage at peptide bonds formed at Pro or Gln residues: Pro95-Pro96, Pro104-Pro105, Pro105-Arg106, Gln110-Gly111, Gln131-Gly132, Pro135-Gln136, Gln136-Gly137, and Gln141-Gly142.

Degradation of acidic PRPs by *S. gordonii* SK12 initially generates a pentapeptide, Arg106Gly107Arg108Pro109Gln110, containing two of the five Arg residues in PRP-1.

The N-terminal Glu1-Pro104Pro105 peptide derived from PRP-1 by *S. gordonii* SK12 lacks the bacterial adhesion-promoting ProGln-terminus, but contains the hydroxyapatite binding domain. Since small phosphorylated proline-rich peptides and PRP-3 display increased affinity for hydroxyapatite surfaces (Moreno E C et al., J Biol Chem 257 (1982) 2981–9; Madapallimattam G & Bennick A, Biochem J 270 (1990) 297–304; Lamkin M S et al., J Dent Res 75 (1996) 803–8), such N-terminal peptides can affect bacterial adhesion by occupying hydroxyapatite sites or altering the pellicle mosaic of binding structures. Proteolytic cleavage is known to unmask hidden binding structures (Gibbons R J et al., Arch Oral Biol 35 Suppl (1990) 107s–114s), and strains of *Actinomyces* species recognize diverse sites in acidic PRPs and statherin (Hallberg K et al., Oral Microbiol Immunol 13 (1998) 327–336; Li T et al., Infect Immun 67 (1999) 2053–9). Furthermore, acidic PRP-degradation generated multiple middle/C-terminal peptides with adhesion-active ProGln-termini, potentially inhibiting the adhesion of oral pathogens binding to acidic PRPs and statherin, i.e. *S. mutans* (Gibbons R J & Hay D I, J Dent Res 68 (1989) 1303–7), *P. gingivalis* (Amano A et al., Infect Immun 62 (1994) 3372–80) and *Fusobacterium nucleatum* (Xie H et al., Oral Microbiol Immunol 6 (1991) 257–63). Commensal and pathogenic species display high and low avidity binding to acidic PRPs, respectively, and may respond differently to ProGln-terminating peptides. Alternatively, both the N-terminal and middle/C-terminal peptides could act as inhibitors or retarders of plaque formation in a broader sense.

While the inventors believe these explanations to be true they are of a hypothetical nature and should not be understood so as to limit the scope of the invention which is only determined by the appended claims.

According to the invention is disclosed an oligopeptide protecting against dental caries comprising two arginine residues selected from the group consisting of pentapeptide, hexapeptide, heptapeptide, octapeptide, nonapeptide and decapeptide. Particularly preferred is the pentapeptide ArgGlyArgProGln.

Also preferred is a penta- to decapeptide comprised by the sequence of amino acid 99 to amino acid 115 of the 150 residue PRP-1 protein: GlyGlyHisProArgProProArgGlyArgProGlnGlyProProGlnGln, SEQ ID No. 13, with the proviso that it contains two or more Arg.

Also preferred are the following peptides:
ArgGlyArgProGln (residues 106–110) SEQ ID No. 1;
ArgGlyArgProGlnGly (residues 106–111) SEQ ID No. 2;
ArgGlyArgProGlnGlyPro (residues 106–112) SEQ ID No. 3;
ArgGlyArgProGlnGlyProPro (residues 106–113) SEQ ID No. 4;
ArgGlyArgProGlnGlyProProGln (residues 106–114) SEQ ID No. 5;
ArgGlyArgProGlnGlyProProGlnGln (residues 106–115) SEQ ID No. 6;
GlyGlyHisProArgProProArgGlyArg (residues 99–108) SEQ ID No. 7;
GlyHisProArgProProArgGlyArg (residues 100–108) SEQ ID No. 8;
HisProArgProProArgGlyArg (residues 101–108) SEQ ID No. 9;
ProArgProProArgGlyArg (residues 102–108) SEQ ID No. 10;
ArgProProArgGlyArg (residues 103–108) SEQ ID No. 11;
ProProArgGlyArg (residues 104–108) SEQ ID No. 12.

Common to SEQ ID Nos. 1–13 is the sequence ProArgGlyArg.

The peptides of the invention can be easily synthesized by solid phase or liquid phase methods known in the art.

According to the invention is disclosed a method of preventing dental caries comprising the oral administration of a prevention-effective amount of an oligopeptide comprising two arginine residues selected from the group consisting of pentapeptide, hexapeptide, heptapeptide, octapeptide, nonapeptide and decapeptide. Particularly preferred is the pentapeptide ArgGlyArgProGln for use in the method of preventing dental caries.

Also preferred for use in the method of preventing dental caries is a penta- to decapeptide comprised by the sequence of amino acid 99 to amino acid 115 of the 150 residue PRP-1 protein: GlyGlyHisProArgProProArgGlyArgProGlnGlyProProGlnGln, SEQ ID No. 13, with the proviso that it contains two or more Arg.

Also preferred for use of preventing dental caries are the following peptides:
ArgGlyArgProGln (residues 106–110) SEQ ID No. 1;
ArgGlyArgProGlnGly (residues 106–111) SEQ ID No. 2;
ArgGlyArgProGlnGlyPro (residues 106–112) SEQ ID No. 3;
ArgGlyArgProGlnGlyProPro (residues 106–113) SEQ ID No. 4;
ArgGlyArgProGlnGlyProProGln (residues 106–114) SEQ ID No. 5;
ArgGlyArgProGlnGlyProProGlnGln (residues 106–115) SEQ ID No. 6;
GlyGlyHisProArgProProArgGlyArg (residues 99–108) SEQ ID No. 7;
GlyHisProArgProProArgGlyArg (residues 100–108) SEQ ID No. 8;
HisProArgProProArgGlyArg (residues 101–108) SEQ ID No. 9;

ProArgProProArgGlyArg (residues 102–108) SEQ ID No. 10;
ArgProProArgGlyArg (residues 103–108) SEQ ID No. 11;
ProProArgGlyArg (residues 104–108) SEQ ID No. 12.

According to the invention is disclosed a composition for preventing dental caries comprising a prevention-effective amount of an oligopeptide comprising two arginine residues selected from the group consisting of pentapeptide, hexapeptide, heptapeptide, octapeptide, nonapeptide and decapeptide, and a suitable carrier. Particularly preferred is the pentapeptide ArgGlyArgProGln SEQ ID No. 1. Suitable carriers include state-of-the-art toothpaste and mouthwash compositions but also chewing-gums, lozenges, and the like.

Also preferred for use in the composition for preventing dental caries is a penta- to decapeptide comprised by the sequence of amino acid 99 to amino acid 115 of the 150 residue PRP-1 protein: GlyGlyHisProArgProProArgGlyArgProGlnGlyProProGlnGln, SEQ ID No. 13, with the proviso that it contains two or more Arg.

Also preferred for use in the composition for preventing dental caries are the following peptides:
ArgGlyArgProGln (residues 106–110) SEQ ID No. 1:
ArgGlyArgProGlnGly (residues 106–111) SEQ ID No. 2:
ArgGlyArgProGlnGlyPro (residues 106–112) SEQ ID No. 3;
ArgGlyArgProGlnGlyProPro (residues 106–113) SEQ ID No. 4;
ArgGlyArgProGlnGlyProProGln (residues 106–114) SEQ ID No. 5;
ArgGlyArgProGlnGlyProProGlnGln (residues 106–115) SEQ ID No. 6;
GlyGlyHisProArgProProArgGlyArg (residues 99–108) SEQ ID No. 7;
GlyHisProArgProProArgGlyArg (residues 100–108) SEQ ID No. 8;
H is ProArgProProArgGlyArg (residues 101–108) SEQ ID No. 9;
ProArgProProArgGlyArg (residues 102–108) SEQ ID No. 10;
ArgProProArgGlyArg (residues 103–108) SEQ ID No. 11;
ProProArgGlyArg (residues 104–108) SEQ ID No 12.

Since the caries-protecting peptides according to the invention are peptides produced by the human body or correspond to sequences thereof they are well tolerated. Optimal caries-protecting amounts of these peptides can be easily determined by experiment because the absence of important toxicity restraints. Single doses from 0.1 mg to 1 g will be appropriate for most applications.

The invention will be better understood by reference to a drawing and the following description of preferred embodiments thereof.

DESCRIPTION OF THE DRAWING

FIG. 3a) or peptide gel filtration (peak 5).

DESCRIPTION OF PREFERRED EMBODIMENTS

EXAMPLE 1

Isolation of Acidic PRPs

Parotid saliva was collected from three subjects homozygous for PRP-1 and PIF-s using Lashley cups and mild acidic lozenge stimulation. After pooling of the salivas and dilution (1:1 by volume) with 50 mmol/L Tris-HCl, 25 mmol/L NaCl, pH 8.0 (Tris-HCl buffer), the saliva sample was subjected to DEAE-Sephacel column chromatography (15×1.6 cm, Pharmacia, Uppsala, Sweden) using a linear gradient of 25 to 1000 mmol/L NaCl in Tris-HCl buffer. The protein fraction containing the acidic PRPs (PRP-1/PIF-s and PRP-3/PIF-f) was concentrated via ultrafiltration using a Centriprep 10 concentrator (Amicon Inc., Beverly, Mass.), and subjected to gel filtration (HiLoad™ 26/60 Superdex S-200 Prep grade column, Pharmacia) in 20 mmol/L Tris-HCl, 500 mmol/L NaCl, pH 8.0. The resolved protein fractions (PRP-1/PIF-s and PRP-3/PIF-f) were dialyzed against Tris-HCl buffer (Spectra/Pore membrane No. 4, Spectrum Medical Industries, Inc., Houston, Tex.). Each protein fraction (PRP-1/PIF-s and PRP-3/PIF-f) was finally purified on a Macroprep high Q column (15×1.6 cm, Bio-Rad, Hercules, Calif.) using a linear gradient of 25 to 1000 mmol/L NaCl in 50 mmol/L Tris-HCl, pH 8.0. The purified proteins were extensively dialyzed against water, lyophilized and stored at –20° C.

EXAMPLE 2

Bacterial Strains and Culturing

The origins and species designations of strains of *Actinomyces naeslundii*, *Actinomyces odontolyticus*, *A. naeslundii* genospecies 1 strain ATCC 12104, genospecies 2 strain T14V, *A. odontolyticus* strain PK984 and *A. viscosus* strain 19246 are as previously described (Hallberg K et al, see above; Hallberg K et al., Oral Microbiol Immunol 13 (1989) 188–192; Li et al., 1999, see above). The strains of *S. anginosus, S. gordonii, S. mitis, S. oralis* and *S. sanguis* (provided by Dr. M. Kilian, Department of Oral Biology, Royal Dental College, Aarhus, Denmark) have been described (Kilian et al., 1989; Hsu et al., 1994). *S. mutans* strains Ingbritt, JBP and NCTC 10449, *S. sobrinus* strain SL-1 and *Porphyromonas gingivalis* strains W83 and ATCC 33277 were provided by Dr. J. Carlsson, Department of Oral Biology, Umeå University, Sweden. All strains were grown overnight on Columbia-II-agar base plates (Becton Dickinson and Company, Cockeysville, Md.), supplemented with 30 ml of a human erythrocyte suspension per liter, at 37° C. in an atmosphere with 5% $CO_2$. Growth of *S. gordonii* strain SK12 identified two morphological types, one forming flat (strain SK12-I) and the other convex (strain SK12-II) colonies. Strain SK12-I (the flat colony-forming type) was selected for the degradation experiments. Neither whole cell soluble protein patterns, as analyzed by SDS-PAGE, nor acidic PRP cleavage patterns distinguished between the two types. The strains intended for degradation experiments were then grown at 37° C. for 18 h in 5 mL trypticase soy bean glucose limiting broth (1.7% peptone, 0.3% soy peptone, 0.15% yeast extract, 12.5 mmol/L glucose, 12.5 mmol/L $NH_4HCO_3$ in 1 mol/L $NaH_2PO_4/K_2HPO_4$ buffer, pH 7.3) in an atmosphere with 5% $CO_2$. The cells were pelleted by centrifugation at 17,000×g for 5 min, washed twice in 0.43% NaCl, 0.042% KCl, 0.1% $Na_2HPO_4$, 0.1% $KH_2PO_4$, 1% glycerophosphate disodium salt, 0.024% $CaCl_2$, and 0.01% $MgCl_2.H_2O$ (M-DIL buffer), re-suspended in M-DIL buffer at a concentration of 2×109 cells/mL. The bacterial cells (and cell-free supernatant after pelleting of bacteria by centrifugation) were kept on ice prior to degradation experiments. The strains intended for adhesion tests were metabolically labeled by adding 35S-methionine (200 *Ci, Tran 35S-Label, ICN Pharmaceuticals Inc., Irvine, Calif.) to bacteria suspended in 100 µL 10 mmol/L $Na_2HPO_4$, $NaH_2PO_4$, 0.137 M NaCl, pH 7.2, (PBS) prior to growth on Columbia-II-agar plates.

EXAMPLE 3

Degradation of Acidic PRPs

Equal volumes (200 µL) of purified protein (0.6 mg/mL) and bacteria (2×109 cells/mL), both dissolved in M-DIL buffer, were mixed and incubated at 37° C. for 15 min, 4 h, 20 h and 1 week. After pelleting of the bacteria by centrifugation at 17,000×g for 10 min, the supernatants were aliquoted, lyophilized and stored at −80° C. prior to analysis. In some experiments, cell free enzyme supernatants and parotid saliva from defined acidic PRP phenotypes were used following the same protocol. The saliva was collected as described above and sterilized by filtering (0.20 µm Minisart filter, Sartorius, Göttingen, Germany).

EXAMPLE 4

Native Alkaline PAGE

Native alkaline polyacrylamide gel electrophoresis was performed essentially as described (Azen and Yu, 1984). The lyophilized supernatants were dissolved in 50 µL sample buffer containing 1% glycine, 10% glycerol and 0.025% bromophenol blue and centrifuged at 17,000×g for 10 min. The electrophoresis was performed using precast Tris-glycine 7.5% resolving gels with 4% stacking gels (Bio-Rad) at 100 V for 20 min followed by 175 V for 1 h 30 min in a buffer containing 0.038 M Tris-glycine, pH 8.4. The gels were stained with 0.1% Coomassie Blue R (Serva Feinbiochemica, Heidelberg, Germany) in 20% trichloroacetic acid (Merck, Darmstadt, Germany) for 16 h, destained in 2% acetic acid for 16 h and finally soaked in water for 2 h.

EXAMPLE 5

Densitometry

The degree of acidic PRP degradation was quantified by densitometry of native alkaline PAGE gels using a Model GS-700 Imaging densitometer and the Molecular Analyst Software (Bio-Rad). The degree of degradation of PRP-1 and PRP-3 was scored from 0 to 5 according to the following criteria: 0 0<10%, 1=10<20%, 2=20<40%, 3=40<60%, 4=60<80%, 5 80<100% reduction of PRP-1 or PRP-3 at 4 h of incubation. In the case of certain strains, score 1 denotes the formation after 20 h of incubation of peptide fragments similar to those generated after 4 h by the strains with a high PRP degradation rate (Table 1).

EXAMPLE 6

Gel Filtration

The lyophilized supernatants obtained by incubation of bacteria with acidic PRPs were dissolved in 200 µL 20 mM Tris-HCl, pH 8.0, containing 0.5 M NaCl and subjected to gel filtration on Superose 12 HR 10/30 or a Superdex Peptide HR10/30 (Pharmacia) columns, equilibrated in 20 mM Tris-HCl, pH 8.0. The flow rate was 0.2 mL/min and the absorbance was monitored at 214 nm. Fractions of 1 mL were collected.

EXAMPLE 7

Hydroxyapatite Assay

Adherence of 35S-methionine labeled bacteria to acidic PRP-1 was measured by the hydroxyapatite assay as previously described (Carlen et al., 1998).

EXAMPLE 8

Mass Spectrometry

All mass spectrometric data were acquired on a hybrid quadrupole time-of-flight (Q-ToF) mass spectrometer (Micromass, Manchester, UK). A Z-configured nano spray source was used and samples were introduced via gold-coated spraying needles (Protana, Odense, Denmark). Detection was all times in the positive ion mode. Needles were opened manually under a light-microscope resulting in an opening of approximately 5 µm. Before analysis, remaining contaminants and salt were removed by applying the samples to nano-columns; Gel-loader tips (Eppendorf, Hamburg, Germany) packed with POROS R3 reverse phase resin (PerSeptive Biosystems, Framingham, Mass., USA) to a bed volume of approximately 200 nL. Normally, 5 µL of sample was applied to the resin followed by washing with approximately 30 µL 0.1% TFA and elution with 60% CH3CN in 1% acetic acid directly into the nano-spray needle.

EXAMPLE 9

N-terminal Sequence Analysis

Edman degradation was performed directly on proteins blotted (Transblot, Bio-Rad) onto PVDF-membranes using an Applied Biosystems 477A pulsed liquid phase sequencer (Foster City, Calif.) with an on-line PTH 120A analyzer. Sequence analysis was performed with cycle programs adapted to the reaction cartridges and chemicals from the manufacturer. Yields were calculated from sequenced standard *-lactoglobulin.

EXAMPLE 10

Substrate Specificity

The substrate specificity of bacterial strains was measured as previously described (Erlanger et al., 1961). Briefly, 25 µL of bacterial suspension (5×109 cells/mL in M-DIL buffer) was diluted with 25 µL of 0.1 mol/L Tris-HCl, pH 7.0, followed by addition of 50 µL of B-Arg-pNA (Sigma, St. Louis, Mo.) and Z-Gly-Pro-pNA (Bachem, Bulendorf, Switzerland) (8.0 mmol/L in DMSO). After incubation at 37° C. for 16 h, the extent of cleavage was measured by the absorbance at 414 nm.

EXAMPLE 11

Figure 1:
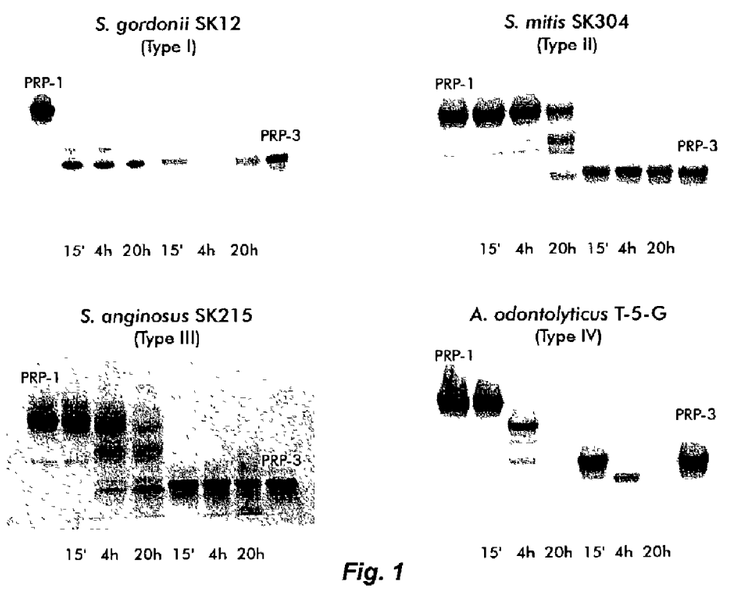
FIG. 1 illustrates the native alkaline PAGE patterns of N-terminal acidic peptides from degradation of acidic PRPs (PRP-1 and PRP-3) by strains of commensal *Streptococcus* and *Actinomyces* species.

Degradation of Acidic PRPs by Commensal *Streptococcus* and *Actinomyces* Species Strains of *Streptococcus* and *Actinomyces* species were tested for degradation of acidic PRPs (PRP-1 and PRP-3) by co-incubation of bacteria and protein followed by native alkaline PAGE (Table 1, FIG. 1). Degradation of PRP-1 occurred with *S. oralis* (1 of 4 strains), *S. mitis* (1 of 4 strains), *S. gordonii* (3 of 4 strains), *S. sanguis* (4 of 4 strains), *S. anginosus* (3 of 4 strains) and *A. odontolyticus* (4 of 7 strains), but not with *S. mutans* (3 strains), *S. sobrinus* (1 strain), *A. naeslundii* genospecies 1 (6 strains) and genospecies 2 (7 strains) or *A. viscosus* (1 strain). *S. gordonii* and *A. odontolyticus* displayed high PRP-1 cleavage rates (scores 4 and 5), while other species had moderate (scores 2 and 3) to low (score 1) cleavage rates. While most species showed high PRP-1 relative to PRP-3 cleavage rates, *A. odontolyticus* displayed equal PRP-1 and PRP-3 cleavage rates. Degradation of PRP-1 also occurred in cell-free supernatants (Table 1), and *S. gordonii* strain SK12 (with a high PRP-1 cleavage rate) degraded PRP-1, PRP-2, Db-s, PIF-s and Pa in parotid saliva from defined donors (data not shown).

Both streptococci adhering to and those not adhering to PRP-1 degraded acidic PRPs (Table 1). While *A. naeslundii* genospecies 1 and 2 bound to but did not degrade acidic PRPs, the opposite was true for *A. odontolyticus*. In addition, both S-IgA1 protease positive and negative strains degraded acidic PRPs (Table 1). Thus, no obvious relationship was found between PRP degradation and adhesion to acidic PRPs or S-IgA1 protease activity.

EXAMPLE 12

Time-Dependency of Acidic PRP Degradation

Figure 3A:
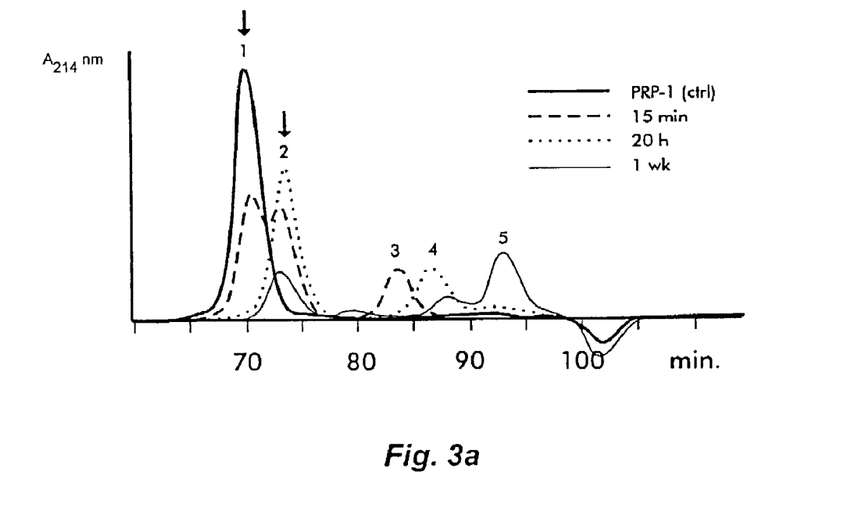
FIG. 3a illustrates the gel filtration patterns of peptide fragments from the degradation of PRP-1 by *S. gordonii* strain SK12 for different time periods.

The native alkaline PAGE patterns from degradation of acidic PRPs for different times indicated a time-dependency of degradation for all strains (FIG. 1). The time-dependency of degradation of PRP-1 by *S. gordonii* strain SK12 was further analyzed by gel filtration of fragments formed after different times of incubation (FIG. 3a). Degradation of PRP-1 (peak 1) for 15 min generated a peptide eluting similar to PRP-3 (peak 2) and later-eluting, smaller peptides (peak 3). Prolonged degradation (20 h) completely converted PRP-1 into the peptide eluting similar to PRP-3 (peak 2) and even later-eluting peptides (peak 4). Even further degradation (1 week) completely transformed all peptides (except for the one eluting similar to PRP-3) into oligopeptides and amino acids (peak 5), as identified using peptide gel filtration (data not shown).

EXAMPLE 13

Identity and Structural Features of Acidic PRP-Derived Peptides

Figure 2:
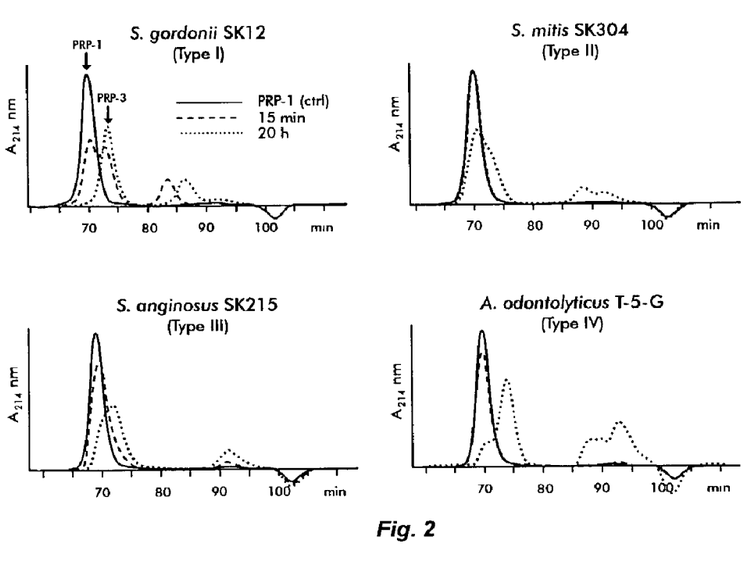
FIG. 2 illustrates the gel filtration patterns of fragments formed by degradation of PRP-1 by strains representative for each of the four degradation patterns identified among streptococci and actinomycetes.
Figure 3B:
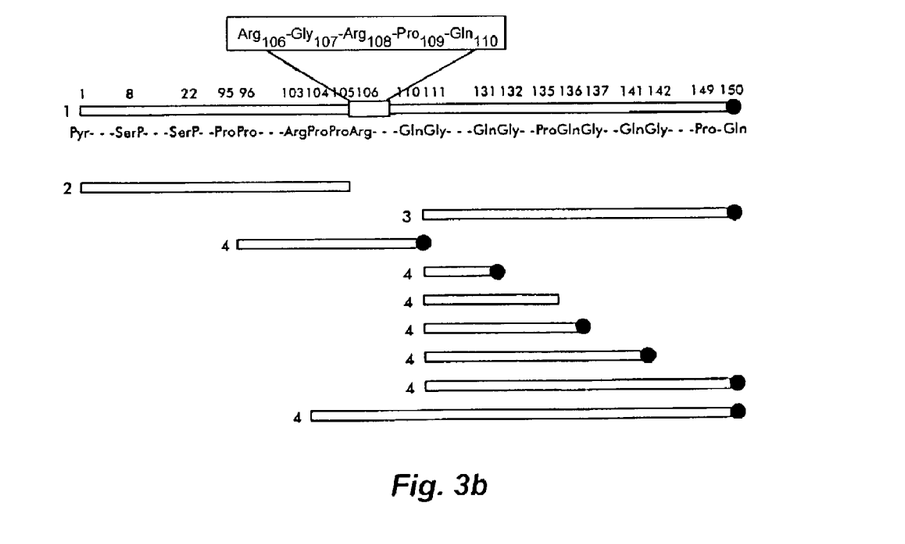
FIG. 3b illustrates the identification by mass spectrometry of fragments separated using either gel filtration (peaks 1–4, cf.

The peptides generated from PRP-1 by *S. gordonii* strain SK12 were identified by mass spectrometry of the peptide peaks obtained by gel filtration (FIGS. 2 and 3). An N-terminal 105 residue peptide Pyr1-Pro104Pro105 (peak 2) and a C-terminal 40 residue peptide Gly111-Pro149Gln150 (peak 3) were identified after initial (15 min) cleavage of PRP-1 (FIG. 3b). A series of 15–47 residue peptides (peak 4; Pro96-Pro109Gln110, Gly111-Pro130Gln131, Gly111-Pro134Pro135, Gly111-Pro135Gln136, Gly111-Pro140Gln141, Gly111-Pro149Gln150 and Pro104-Pro149Gln150) were identified after prolonged degradation (20 h). In addition, a pyroglutamatic acid, Pyr, was found at the N-terminal residues of PRP-1 and PRP-3 (FIG. 3b), explaining our difficulties in sequencing of N-terminal fragments by Edman degradation.

EXAMPLE 14

Patterns of Acidic PRP Degradation

The peptide profiles displayed by native alkaline PAGE distinguished four major degradation patterns, I–IV (Table 1, FIG. 1). While all four patterns contained N-terminal peptides migrating close to PRP-3, the peptide banding patterns were unique to a particular strain or species (FIG. 1, Table 1). Both species specific (*A. odontolyticus* and *S. gordonii*) and multiple patterns within a species (*S. anginosus* and *S. sanguis*), as well as a sharing of patterns between species, were observed. In addition, gel filtration of the degradation products obtained by a strain representative of each pattern verified somewhat deviating profiles, containing large (70–75 min retention) and intermediate (80–95 min retention) peptides (FIG. 1b). To investigate the substrate specificities associated with acidic PRP degradation, strains representative of each degradation pattern were tested for truncation of Pro- and Arg-containing chromogenic substrates. The strains did not cleave Z-Gly-Pro-pNA, which is a substrate for prolyl endoproteases (Blumberg et al., 1980), or B-Arg-pNA, while *P. gingivalis* strain ATCC 33277 cleaved both substrates.

EXAMPLE 15

Lozenge

A solution of ArgGlyArgProGln (SEQ ID No. 1) 'acetate' was prepared by dissolving ArgGlyArgProGln in water and adding acetic acid to pH 6.5. The aqueous solution was freeze-dried and the powder thereby obtained mixed with 150 g of polyethylene glycol 8000, 150 g of microcrystalline cellulose, 600 g of mannitol, 10 g of stearic acid are milled to pass a 40 mesh sieve. The mixture is fed to a tablet press to produce 1 g tablets.

EXAMPLE 16

Chewable Tablet 900 g mannitol and 5 g sodium saccharin are screened through a 40-mesh screen and blended thoroughly with 40 g ArgGlyArgProGln acetate (SEQ ID No. 1 acetate) prepared as described above. A binder solution of 20 g of acacia and 50 g of gelatin in 500 ml water was prepared separately. The powder was wet granulated using 200 ml of binder solution for 1000 powder. After drying overnight at 75° C. the granules were screened through a 12 mesh screen, mixed with 1 g of peppermint oil adsorbed on 3 g of colloidal silica and 25 g magnesium stearate. From this mixture 1 g tablets were compressed to a hardness of 12 kg.

EXAMPLE 17

Toothpaste

A suitable toothpaste base for incorporating the compounds of the invention is described in U.S. Pat. No. 3,935,305 (Delaney et al.) which is incorporated herein by reference; in particular, see Example 1. A suitable amount of ArgGlyArgProGln acetate (for preparation, see above) is 1% by weight of base.

EXAMPLE 18

Mouthwash

A suitable mouthwash base for incorporating the compounds of the invention is described in U.S. Pat. No. 5,145,664 (Thompson) which is incorporated herein by reference; see Example 1. A suitable amount of ArgGlyArgProGln acetate (for preparation, see above) is 1% by weight of base.

LEGENDS TO FIGURES

FIG. 1. Native alkaline PAGE patterns of N-terminal acidic peptides from degradation of acidic PRPs (PRP-1 and PRP-3) by strains of commensal *Streptococcus* and *Actinomyces* species. Shown are the degradation patterns of strains representative for each of the four degradation patterns (I–IV) identified among isolates of streptococci and actinomycetes (cf. Table 1). All strains (Table 1) were co-incubated with purified PRP-1 and PRP-3 for different times (15 min, 4 h and 20 h) and analyzed for such peptide patterns.

FIG. 2. Gel filtration patterns of fragments formed by degradation of PRP-1 by strains representative for each of the four degradation patterns identified among streptococci and actinomycetes (cf. Table 1). The strains were incubated with PRP-1 for 15 min and 20 h. The retention times of purified PRP-1 and PRP-3 are indicated by vertical arrows.

FIG. 3a. Gel filtration patterns of peptide fragments from degradation of PRP-1 by *S. gordonii* strain SK12 for different times. The numbering of the peaks refer to mass spectrometric identification of the corresponding peptide structures (cf. FIG. 3b). The vertical arrows denote the retention times of purified PRP-1 and PRP-3.

FIG. 3b. Identification by mass spectrometry of fragments separated using either gel filtration (peaks 1–4, cf. FIG. 3a) or peptide gel filtration (peak 5). The numbering of peptides by letters A–G denotes the corresponding signals in the mass spectrum. Pyr indicates a pyroglutamic acid. The mass numbers with an asterisk indicate average masses from de-convoluted mass spectra, while unlabeled mass numbers are consistent with the monoisotopic mass of the peptide.

TABLE 1

Degradation of acidic PRPs by *Streptococcus* and *Actinomyces* species

| Species[a] | Strain[a] | Acidic PRP degradation[b] | | | PRP-1 adhesion[d] | IgA1 protease[e] |
|---|---|---|---|---|---|---|
| | | PRP-1 | PRP-3 | Type[c] | | |
| *S. gordonii* | SK 12, SK 184 | 5 | 1 | I | − | − |
| | SK 120 | 5 | 0 | I | + | − |
| | SK 33 | 0 | 0 | — | − | − |
| *S. sanguis* | SK 85 | 4 | 0 | I | − | + |
| | SK 112 | 2 | 1 | II | + | + |
| | SK 37 | 2 | 1 | II | − | + |
| | SK 162 | 2 | 1 | III | − | + |
| *S. mitis* | SK 304 | 1 | 0 | II | − | − |
| | SK 305 | 0 | 0 | — | + | − |
| | SK 96, SK 142 | 0 | 0 | — | − | − |
| *S. anginosus* | SK 215 | 3 | 1 | III | − | − |
| | SK 52 | 1 | 1 | II | − | − |
| | SK 63 | 1 | 0 | II | − | − |
| | SK 218 | 0 | 0 | — | − | − |
| *S. oralis* | SK 143 | 1 | 0 | IV | − | + |
| | SK 2, SK 92 | 0 | 0 | — | − | + |
| | C104 | 0 | 0 | — | nt | + |
| *S. mutans* | Ingbritt, JBP | 0 | 0 | — | − | nt |
| | NCTC 10449 | 0 | 0 | — | nt | nt |
| *S. sobrinus* | SL-1 | 0 | 0 | — | nt | nt |
| *A. odontolyticus* | T-5-G | 5 | 5 | IV | + | nt |
| | T-1-K | 2 | 1 | IV | − | nt |
| | T-23-N, T-3-G | 1[b] | 1 | IV | − | nt |
| | T-21-N, T-22-N, PK984 | 0 | 0 | — | − | nt |
| *A. naeslundii* genospecies 1 | | | | | | |
| | ATCC 12104, P-3-N, P-5-N, P-11-N, B-2-G, PK947 | 0 | 0 | — | − | nt |
| *A. naeslundii* genospecies 2 | | | | | | |
| | T14V, P-1-N, P-7-N, P-1-K, P-1-G, B-7-N, P-2-N | 0 | 0 | — | + | nt |

TABLE 1-continued

Degradation of acidic PRPs by *Streptococcus* and *Actinomyces* species

| Species[a] | Strain[a] | Acidic PRP degradation[b] | | PRP-1 Type[c] | PRP-1 adhesion[d] | IgA1 protease[e] |
|---|---|---|---|---|---|---|
| | | PRP-1 | PRP-3 | | | |
| A. viscosus | 19246 | 0 | 0 | — | − | nt |
| P. gingivalis | W83 | 5 | 5 | — | − | + |

[a]The sources of the strains are given above.
[b]Acidic PRP degradation was carried out by co-incubation of PRP-1 or PRP-3 and bacteria for 15 min, 4 h and 20 h followed by native alkaline PAGE (FIG. 1). The degree of cleavage at 4 h was scored from 0 to 5 by densitometry: 0 = 0 < 10%, 1 = 10 < 20%, 2 = 20 < 40%, 3 = 40 < 60%, 4 = 60 < 80%, and 5 = 80 < 100% loss of acidic PRPs. Score 1 labeled with a superscript denotes the formation of degradation products.
Cells free supernatant resulted in similar degradation patterns for most strains. 95% confidence intervals of densitometric runs corresponded to 8% of mean.
[c]The strains were classified into degradation patterns I–IV based on native alkaline PAGE peptide profiles (FIG. 1). The type-I pattern displayed a peptide migrating just below PRP-3; The type-II pattern a peptide migrating just below PRP-3 and another between PRP-1 and PRP-3; The type-III pattern two peptides migrating just below and above PRP-3, one between PRP-1 and PRP-3 and a fourth just below PRP-1; and the type-IV pattern a peptide migrating identical to PRP-3 and another between PRP-1 and PRP-3 although closer to PRP-1 compared to patterns II and III.
[d]Adhesion of $^{35}$S-labeled bacteria to PRP-1-coated hydroxyapatite beads. Adhesion exceeding 15% of added cells was considered positive. Adhesion of Actinomyces was tested at 5 μg/ml of PRP-1 and for other bacteria at 30 μg/ml of PRP-1. The criteria for positive binding and assay conditions differ from those in other studies of adhesion of streptococci and *P. gingivalis* (Hsu et al., 1994).
[e]S-IgA protease activity of commensal streptococci (Kilian et al., 1989), *P. gingivalis* (Kilian, 1981) and *Actinomyces* species, which lack S-IgA1 protease activity (M. Kilian, personal communication).

TABLE 2

Simplified map of generated peptides in comparison with PRP-1.

| Peak | Peptide | Mass (Da) |
|---|---|---|
| 1 | Pyr1-Pro149-Gln150 | 15 514.0* |
| 2 | Pyr1-Pro104-Pro105 | 11 005.5* |
| 3 | Gly111-Pro149-Gln150 | 3 930.0 |
| 4 | Pro96-Pro109-Gln110 (A) | 1 663.7 |
| 4 | Gly111-Pro130-Gln131 (B) | 2 082.1 |
| 4 | Gly111-Pro134-Pro135 (C) | 2 430.4 |
| 4 | Gly111-Pro135-Gln136 (D) | 2 558.4 |
| 4 | Gly111-Pro140-Gln141 (E) | 3 053.6 |
| 4 | Gly111-Pro149-Gln150 (F) | 3 930.0 |
| 4 | Pro104-Pro149-Gln150 (G) | 4 718.3 |
| 5 | Oligopeptides/amino acids | |

The potential cleavage sites at peptide bonds formed at Pro or Gln residues are given. The presumed Arg-containing pentapeptide is blown up, ProGln-termini are marked by black circles and the post-translational cyclization of the N-terminal Glu residue to a pyroglutamic acid residue is marked Pyr. The verification by mass spectrometry of phosphorylation of Ser at positions 8 and 22 is marked.

What is claimed is:

1. An oligopeptide having dental caries protective properties selected from the group consisting of SEQ ID Nos. 1 through 13.

2. The oligopeptide of claim 1 which is SEQ ID No. 13.

3. The oligopeptide of claim 1 which is SEQ ID No. 1.

4. The oligopeptide of claim 1 selected from the group consisting of SEQ ID Nos. 2 through 12.

5. A method of preventing dental caries comprising the oral administration of a dental caries prevention-effective amount of the oligopeptide of claim 1.

6. A composition for preventing dental caries comprising a dental caries prevention-effective amount of the oligopeptide of claim 1 and a carrier therefor.

7. The composition of claim 6 wherein the carrier is selected from the group consisting of toothpaste, mouthwash, chewing-gum, lozenge, chewable tablets.

8. A method of preventing dental caries comprising the oral administration of a dental caries prevention-effective amount of the peptide of claim 2.

9. A method of preventing dental caries comprising the oral administration of a dental caries prevention-effective amount of the peptide of claim 3.

10. A method preventing caries comprising the oral administration of a dental caries prevention-effective amount of the peptide of claim 4.

11. A composition for preventing dental caries comprising a dental caries prevention-effective amount of the oligopeptide of claim 2 and a carrier therefor.

12. A composition for preventing dental caries comprising a dental caries prevention-effective amount of the oligopeptide of claim 3 and a carrier therefor.

13. A composition for preventing dental caries comprising a dental caries prevention-effective amount of the oligopeptide of claim 4 and a carrier therefor.

14. The composition of claim 7 in which the amount of the oligopeptide is 0.1 mg to 1 gram.

15. The composition of claim 6 in which the amount of the oligopeptide is 0.1 mg to 1 gram.

16. The oligopeptide of claim 1 selected from the group consisting of SEQ ID Nos. 2, 4 and 5.

17. A composition for preventing dental caries comprising 0.1 mg to 1 gram of an oligopeptide selected from the group consisting of SEQ ID Nos. 1–13 and a carrier therefor.

18. A method of preventing dental caries comprising the oral administration of a composition of claim 17.

19. The method of claim 18 wherein the carrier is selected from the group consisting of toothpaste, mouthwash, chewing gum, lozenge and chewable tablet.

20. The composition of claim 17 wherein the carrier is selected from the group consisting of toothpaste, mouthwash, chewing gum, lozenge and chewable tablet.

* * * * *